US008753844B2

(12) United States Patent
Elisashvili et al.

(10) Patent No.: US 8,753,844 B2
(45) Date of Patent: Jun. 17, 2014

(54) OVERPRODUCTION OF LIGNINOLYTIC ENZYMES

(75) Inventors: Vladimir Elisashvili, Tbilisi (GE); Eva Kachlishvili, Tbilisi (GE); Tamas Torok, Richmond, CA (US)

(73) Assignee: The Regents of The University of California, Oakland, CA (US)

( * ) Notice: Subject to any disclaimer, the term of this patent is extended or adjusted under 35 U.S.C. 154(b) by 39 days.

(21) Appl. No.: 13/464,681

(22) Filed: May 4, 2012

(65) Prior Publication Data

US 2012/0295324 A1 Nov. 22, 2012

Related U.S. Application Data

(60) Provisional application No. 61/483,329, filed on May 6, 2011.

(51) Int. Cl.
*C12P 1/02* (2006.01)
*C12N 1/14* (2006.01)
*C12N 9/02* (2006.01)

(52) U.S. Cl.
USPC .......................... 435/71.1; 435/171; 435/189

(58) Field of Classification Search
None
See application file for complete search history.

(56) References Cited

U.S. PATENT DOCUMENTS

| | | | |
|---|---|---|---|
| 5,153,121 A | 10/1992 | Aster et al. | |
| 5,403,723 A | 4/1995 | Call | |
| 5,972,672 A | 10/1999 | Moukha et al. | |
| 6,395,534 B1 | 5/2002 | Raghukumar et al. | |
| 7,732,178 B2 | 6/2010 | Paloheimo et al. | |
| 2006/0104939 A1 | 5/2006 | Covington et al. | |

FOREIGN PATENT DOCUMENTS

| | | |
|---|---|---|
| KR | 1020000031536 | 6/2000 |
| KR | 1020000043999 | 7/2000 |
| KR | 100866999 | 10/2008 |
| WO | WO02079454 | 10/2002 |
| WO | WO2006114787 | 2/2006 |

OTHER PUBLICATIONS

Bailey et al., Interlaboratory testing of methods for assay of xylanase activity, J. Biotechnology, vol. 23, pp. 257-270, 1992.
Elisashvili & Kachlishvili, Physiological regulation of laccase and manganese peroxidase production by white-rot Basidiomycetes, J. Biotechnology, vol. 144, pp. 37-42, 2009.
Galhaup et al., Increased production of laccase by the wood-degrading basidiomycete Trametes pubescens, Enzyme Microb. Technol., vol. 30, pp. 529-536, 2002.
Ghose, Measurement of cellulose activites, Pure Appl. Chem. vol. 59, pp. 257-268. 1987.
Gil & Arora, Effect of culture conditions on manganese peroxidase production and activity by some white rot fungi, J. Ind. Microbiol. Biotechnol., vol. 30, pp. 28-33, 2003.
Lisova et al., Two laccase isoforms of the basidiomycete Cerrena unicolor VKMF-3196. Induction, isolation and properties, J. Basic Microbiol., vol. 50, pp. 72-82, 2010.
Rogalski et al., Immobilization of laccase from Cerrena unicolor on controlled porosity glass, J. Mol. Catalysis B: Enzymatic, vol. 6, pp. 29-39, 1999.
Wariishi et al., Manganese(II) oxidation by manganese peroxidase from the basidiomycete *Phanerochaete chrysosporium*. Kinetic mechanism and role of chelators, J. Biol. Chem., vol. 267, pp. 23688-23695, 1992.
Powerpoint slides presented by Vladimir Elisashvili at Pacific Rim Summit on Industrial Biotechnology and Bioenergy (Honolulu, HI) on Nov. 10, 2009.
Presentation by Vladimir Elisashvili at Pacific Rim Summit on Industrial Biotechnology and Bioenergy (Honolulu, HI) on Nov. 10, 2009.

*Primary Examiner* — Suzanne M Noakes
*Assistant Examiner* — Jae W Lee
(74) *Attorney, Agent, or Firm* — Knobbe, Martens, Olson & Bear LLP

(57) ABSTRACT

Methods, compositions, and systems for overproducing ligninolytic enzymes from the basidiomycetous fungus are described herein. As described, the method can include incubating a fungal strain of Cerrena unicolor IBB 303 in a fermentation system having growth medium which includes lignocellulosic material and then cultivating the fungal strain in the fermentation system under conditions wherein the fungus expresses the ligninolytic enzymes. In some cases, the lignocellulosic material is mandarin peel, ethanol production residue, walnut pericarp, wheat bran, wheat straw, or banana peel.

14 Claims, 3 Drawing Sheets

OVERPRODUCTION OF LIGNINOLYTIC ENZYMES

RELATED APPLICATIONS

The present application claims priority under 35 U.S.C. §119(e) to U.S. Provisional Application No. 61/483329, filed May 6, 2011. This priority application is herein expressly incorporated by reference in its entirety.

STATEMENT OF GOVERNMENT RIGHTS

This invention was made with government support under Contract No. DE-ACO2-05CH11231 awarded by the U.S. Department of Energy and through DOE/NNSA GIPP program CRADA with Verenium Corp. (formerly Diversa Corp.); Subcontract # CRADA (BG0301700) STCU P196. The government has certain rights in the invention.

FIELD OF THE INVENTION

The present invention relates to various fields in biotechnology including the pulp and paper, food, textile, and dye industries, as well as in cosmetics, biochemistry, microbiology, molecular biology, biofuel production, and environmental bioremediation. More specifically, the present invention relates to methods, compositions, and systems for overproducing ligninolytic enzymes.

BACKGROUND

The ligninolytic enzymes of the fungi basidiomycetes are useful for conversion of plant biomass and have numerous industrial applications. Lignin is a biopolymer component of plant cell walls degraded by ligninolytic enzymes (ligninases). In particular, white-rot basidiomycetes secrete one or more extracellular enzymes important for lignin degradation: lignin peroxidase, manganese-dependent peroxidase (MnP), and laccase. However, current technology is limited to producing unsuitably low yields of ligninolytic enzymes at high commercial cost.

SUMMARY OF THE INVENTION

Embodiments of the present disclosure relate to methods, compositions, and systems for overproducing ligninolytic enzymes by growing fungi under conditions that promote expression of ligninolytic enzymes at high yields.

Some embodiments are directed to a method of producing ligninolytic enzymes including incubating a fungal strain capable of expressing these enzymes in a fermentation system that includes growth medium and lignocellulosic material. In some embodiments, the fungal strain is *Cerrena unicolor* or more particularly *Cerrena uniclor* IBB 303. In some embodiments, the fermentation system is a submerged fermentation system. In some embodiments, the lignocellulosic material is mandarin peel, ethanol production residue, walnut pericarp, wheat bran, wheat straw, or banana peel.

In various aspects of the aforementioned method, the ligninolytic enzymes include cellulase, xylanase, laccase, and manganese-dependent peroxidase. In some embodiments, the ligninolytic enzyme is laccase having an activity of 100,000 to 1,000,000 IU/l. In some embodiments, the ligninolytic enzyme is MnP having an activity of 2,000 to 9,000 IU/l.

In some embodiments, the lignocellulosic material is mandarin peel and expression of laccase is enriched among the expressed ligninolytic enzymes. In some embodiments, the lignocellulosic material is walnut pericarp and expression of manganese-dependent peroxidase is enriched among the expressed ligninolytic enzymes.

In some embodiments, the aforementioned method further includes inoculating a starter culture with the fungus. In some embodiments, the method further includes recovering the ligninolytic enzymes from said submerged fermentation system. Various aspects of the method further include co-cultivating the fungal strain with another fungus such as *Trichoderma* sp.

In some embodiments, the growth medium further includes glycerol wherein expression of laccase and manganese-dependent peroxidase is enriched while expression of cellulase and xylanase is repressed. In some embodiments, the growth medium further includes 2,4,6-trinitrotoluene and expression of laccase is enriched among the expressed ligninolytic enzymes.

Some embodiments are drawn to a growth medium for inducing production of ligninolytic enzymes in *C. unicolor* including a carbon source, a nitrogen source, an inorganic salt, yeast extract, and lignocellulosic material. In some embodiments, the carbon source includes glucose, the nitrogen source includes ammonium nitrate, the inorganic salt is a potassium or magnesium cation, and the lignocellulosic material includes mandarin peel, ethanol production residue, walnut pericarp, wheat bran, wheat straw, and/or banana peel.

Various embodiments relate to a submerged fermentation system for producing ligninolytic enzymes including a cultivation vessel; a fungal strain of *C. unicolor* capable of expressing ligninolytic enzymes; growth medium comprising glucose, ammonium nitrate or ammonium sulfate or peptone, a potassium or magnesium cation salt, and lignocellulosic material selected from mandarin peel, ethanol production residue, walnut pericarp, wheat bran, wheat straw, and banana peel; a temperature control device; and an agitation device configured to mix contents in the cultivation vessel.

DETAILED DESCRIPTION

Figure 1:
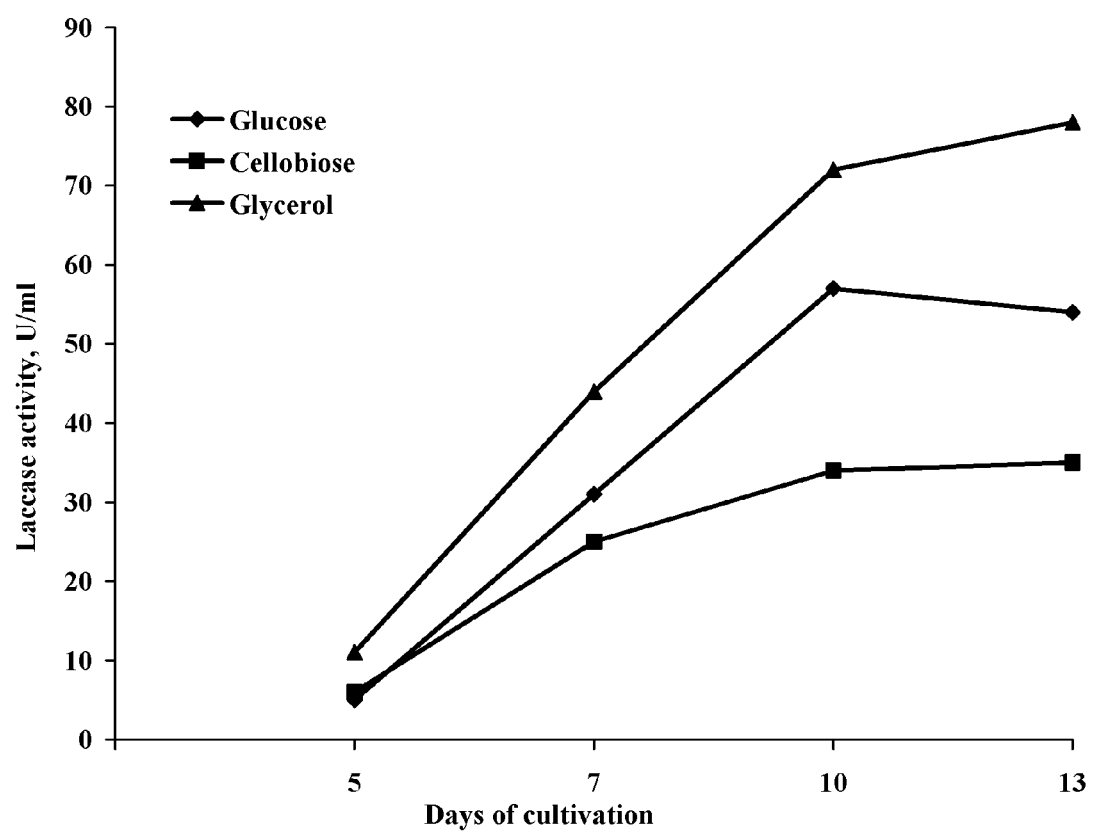
FIG. 1 is a graph showing *Cerrena unicolor* laccase activity in submerged cultivation in the presence of chemically pure carbon sources.

The description that follows illustrates embodiments of the subject matter disclosed herein. Those of skill in the art will recognize that there are numerous variations and modifications of the subject matter provided herein that are encompassed by its scope. Accordingly, the description of certain embodiments should not be deemed to limit the scope of the present invention.

Embodiments disclosed herein relate to methods, compositions, and systems for producing high yields of ligninolytic enzymes (ligninases) from fungus. Ligninases can be produced by incubating fungus in a submerged fermentation system and cultivating the fungus in the presence of lignocellulosic material under conditions that promote expression of ligninases at high levels. Various embodiments relate to growth media capable of promoting fungi to overproduce ligninases at unexpected and hitherto unachievable yields.

Submerged fermentation systems for cost-efficiently achieving high yield production of ligninases are described.

The methods, compositions, and systems for producing ligninolytic enzymes from fungus described herein are useful in a number of industrial applications. For example, embodiments disclosed herein have application in bioremediation of industrial waste streams polluted by hazardous xenobiotics; bio-bleaching and bio-pulping; the textile and dye industries; biotransformation of pharmaceutical and other intermediates; the food industry; biosensor construction; cosmetics; medicine; and analytic biochemistry. These biotechnological applications require large amounts of enzyme at low cost. However, the enzymes presently being investigated are still expensive due to the low yield and high cost in their production and isolation. In addition, although many recombinant organisms efficiently overproduce various industrial enzymes, significant expression of laccase and peroxidases in heterologous systems has not been achieved and therefore, the enzymes are obtained from natural sources.

White-rot basidiomycetes are unique in their ability to degrade all components of lignocellulose due to their capability of synthesizing the relevant hydrolytic and oxidative extracellular enzymes. These fungi secrete one or more of three extracellular enzymes important for lignin degradation: lignin peroxidase (LiP) (EC 1.11.1.14), manganese-dependent peroxidase (manganese peroxidase) (MnP) (EC 1.11.1.13), and laccase (EC 1.10.3.2). Large yields of ligninases can be generated by cultivating fungus in a submerged fermentation system under conditions that optimize fungal expression of the ligninases. The present inventors have discovered that cultivating fungus in the presence of lignocellulosic material under optimum conditions can induce overexpression of ligninases at unexpectedly high yields. In some embodiments, white-rot basidiomycetes fungus is cultivated for ligninases overexpression.

Non-limiting examples of fungi that can be used in the process disclosed herein include the white-rot fungi, such as *Trametes versicolor*, *Phanerochaete chrysosporium*, *Phlebia radiata*, *Funalia trogii*, and *Cerrena unicolor*, which produce laccase and/or manganese peroxidase and/or lignin peroxidase. In some embodiments, the fungus cultivated to overproduce ligninases is *Cerrena unicolor* IBB 303, a novel strain the present inventors isolated from an ecological niche in Georgia.

As used herein, the term "submerged fermentation" refers to fermentation in solution, as opposed to on a solid surface. In various embodiments, a submerged fermentation system includes control of factors such as pH, temperature, oxygen and nitrogen diffusion, gas distribution, and nutrient distribution throughout the fluid fermentation mixture. This may be achieved with agitation and/or mechanical mixing. In various embodiments, a submerged fermentation system includes a cultivation vessel such as flask, tank, vat, or bioreactor optionally having temperature control and/or mechanical mixing means such as a stirrer or shaker. It will be understood that surface or solid fermentation can be used in place of submerged fermentation in any of the embodiments described herein.

In some embodiments, ligninolytic enzymes are produced by incubating fungus in a submerged fermentation system including growth medium. As used herein, the terms "growth medium," "cultivation medium," and "fermentation medium" are used interchangeably. The growth medium can contain a carbon source, a nitrogen source, an inorganic salt, yeast extract, and/or lignocellulosic material. A wide range of carbohydrates including pentoses, hexoses and polysaccharides can be used as a carbon source. Non-limiting examples of carbon sources that can be used in growth medium include Avicel, carboxymethylcellulose (CMC), xylan, glucose, cellobiose, lactose, and glycerol. The concentration of each carbon source in the growth medium can range from about 1, 5, 10, 15, 20, 25, 30, 35, 40, 45, 50, 55, 60, 65, 70, 75, 80, 85, 90, 95, or to about 100 g/l, or any number in between any of the aforementioned concentrations. In some embodiments, the concentration of each carbon source in the growth medium can range from 30 g/l to 80 g/l for cultivation of *Cerrena unicolor* IBB 303.

Non-limiting examples of a nitrogen source include ammonium nitrate, ammonium sulphate, or peptone; optionally in combination with yeast extract. The concentration of each nitrogen source in the growth medium can range from about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or to about 10.0 g/l or any number in between any of the aforementioned concentrations. In some embodiments, the concentration of each nitrogen source in the growth medium can range from 0.5 to 5.0 g/l for cultivation of *Cerrena unicolor* IBB 303.

Non-limiting examples of inorganic salts that can be incorporated in the growth medium include potassium, magnesium, phosphate, sulphate and chloride salts. The concentration of each inorganic salt in the growth medium can range from about 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, or to about 5.0 g/l or any number in between any of the aforementioned concentrations. In some embodiments, the concentration of each salt in the growth medium can range from 0.2 g/l to 1.0 g/l for cultivation of *Cerrena unicolor* IBB 303.

As used herein, "lignocelluosic material" refers to any lignocellulose-containing material. It will be understood that the lignocellulose-containing material may also comprise other constituents, such as cellulose, hemicellulose, and may also comprise constituents such as sugars. Lignocelluosic material can be found, for example, in wood, stems, leaves, branches, hulls, husks, and cobs of plants or trees. Lignocellulosic material also includes herbaceous material, agricultural residue, forestry residue, municipal solid waste, paper waste, and pulp and paper mill residue. Additionally, lignocellulosic material may be in the form of plant cell wall material containing lignin, cellulose, and hemicellulose in a mixed matrix.

In some embodiments, the lignocellulosic material is mandarin peel, ethanol production residue (EPR), walnut pericarp, wheat bran, wheat straw, banana peel, tree leaves, or combinations thereof. The concentration of each lignocellulosic material in the growth medium can range from about 1, 5, 10, 15, 20, 25, 30, 35, 40, 45, 50, 55, 60, 65, 70, 75, 80, 85, 90, 95, 100, 125, 150, 175, or to about 200 g/l or any number in between any of the aforementioned concentrations. In some embodiments, the concentration of each lignocellulosic material can range from 30 g/l to 80 g/l for cultivation of *Cerrena unicolor* IBB 303.

In some embodiments for producing a high yield of laccase, mandarin peel and/or ethanol production residue (EPR) can be used as lignocellulosic material in the cultivation processes described herein. In other embodiments for producing a high yield of manganese-dependent peroxidase, walnut pericarp can be used as lignocellulosic material in the cultivation processes described herein. To generate a high yield of endoglucanase and/or xylanase, mandarin peel, ethanol production residue (EPR), and/or walnut pericarp can be used as lignocellulosic material in certain embodiments.

Growth medium can be supplemented with additional stimulators of ligninase production. Non-limiting examples of additional stimulators which can be added to the growth medium described herein include copper and/or aromatic compounds such as 2,4,6-trinitrotoluene, 2,6-dimethylphenol, ferulic acid, hydroquinone, pyrogallol, vanillin, vanillic acid, and xylidine. In some embodiments, ligninase production is enhanced by cultivation of a fungus, such as *Cerrena unicolor*, with another fungus. In certain embodiments, *Cerrena unicolor* is co-cultivated with *Trichoderma* sp.

In various embodiments, prior to cultivating a fungus by submerged fermentation, a starter culture (pre-culture) of the fungus is generated by inoculating a liquid nutrient medium with a mycelium of the fungus grown, for example, on the surface of an agar plate. The liquid nutrient medium of the starter culture may include any suitable combination of carbon and nitrogen source, for example glucose, ammonium nitrate, and yeast extract. For example, flasks containing 100 ml of nutrient medium can be inoculated from surface agar culture (in a Petri dish) and cultivated on an orbital shaker at 150 rpm and 27° C. After 5-6 days the starter culture can be homogenized in a Waring laboratory blender and the mycelium homogenate can be transferred into sterile medium in the proportion 1:10-1:20. In some embodiments, the mycelium is grown in the form of pellets, which can be 0.5 to 5 mm in diameter.

In some embodiments, fungus is cultivated by submerged fermentation in growth medium described herein under controlled conditions. Culturing can be performed with agitation of the medium, which may be performed mechanically. The level of agitation can be chosen so as to permit the formation of mycelial pellets of average diameter 0.5 mm to 5 mm, while limiting the shearing stresses undergone by the fungus biomass. This level may vary during the culture period.

The temperature at which the fungus is cultivated by submerged cultivation can range from about 15.0° C., 16.0° C., 17.0° C., 18.0° C., 19.0° C., 20.0° C., 21.0° C., 22.0° C., 23.0° C., 24.0° C., 25.0° C., 26.0° C., 27.0° C., 28.0° C., 29.0° C., or to about 30.0° C. or any number in between any of the aforementioned temperatures. In some embodiments, cultivation of *Cerrena unicolor* IBB 303 occurs at a temperature of approximately 27.0° C.

In some embodiments, fungus is cultivated by submerged cultivation in growth medium for numerous days. Culturing can occur for about 1, 2, 3, 4, 5, 6, 7, 8, 9, 10, 11, 12, 13, 14, 15, 16, 17, 18, 19, 20, to about 21 days. It will be understood that the number of days of cultivation can be chosen so as to maximize the amount of enzyme produced. In some embodiments, cultivation of *Cerrena unicolor* IBB 303 occurs for 7-14 days.

Various embodiments relate to enriching overproduction of particular ligninases depending on the lignocelluosic material present in the growth medium. Thus, it is possible to obtain enzyme cocktails, which predominate either in laccase or in manganese-dependent peroxide. For example, the laccase to manganese-dependent peroxidase ratio can be manipulated to favor increased production of laccase. In some embodiments, increased production of laccase relative to manganese-dependent peroxidase can be achieved by cultivating fungus by submerged culturing in growth medium containing ethanol production residue (EPR) as a source of lignocelluosic material. In such embodiments, ethanol production residue (EPR) is present at a concentration range of about 1, 5, 10, 15, 20, 25, 30, 35, 40, 45, 50, 55, 60, 65, 70, 75, 80, 85, 90, 95, 100, 125, 150, 175, or to about 200 g/l or any number in between any of the aforementioned concentrations. In some embodiments, the concentration of ethanol production residue (EPR) for promoting enriched production of laccase by *Cerrena unicolor* IBB 303 can range from 30 g/l to 60 g/l.

In some embodiments, enriched production of manganese-dependent peroxidase relative to laccase can be achieved by cultivating fungus by submerged cultivation in growth medium containing walnut pericarp as a source of lignocelluosic material. In such embodiments, walnut pericarp is present at a concentration range of about 1, 5, 10, 15, 20, 25, 30, 35, 40, 45, 50, 55, 60, 65, 70, 75, 80, 85, 90, 95, 100, 125, 150, 175, or to about 200 g/l or any number in between any of the aforementioned concentrations. In some embodiments, the concentration of walnut pericarp for promoting enriched production of manganese-dependent peroxidase can range from 30 g/l to 80 g/l, and can include about 40 g/l for cultivation of *Cerrena unicolor* IBB 303.

Enzyme preparations lacking hydrolases can be obtained by culturing fungi in the presence of glycerol or glucose at a concentration of between 10 g/l and 25 g/l, and preferably about 15 g/l for cultivation of *Cerrena unicolor* IBB 303.

After the fungus has been cultivated for the desired amount of time, the spent medium contains the ligninases overproduced and secreted by the fungus. Thus, enzyme cocktails more or less enriched in laccase or manganese peroxidase can be used directly from the growth medium supernatant. Alternatively, the overproduced ligninases can be recovered by a variety of protein purification and concentration techniques available in the art. For example, the overproduced ligninases may conveniently be recovered from the spent medium by separating the cells from the medium by centrifugation or filtration, precipitating proteins by means of a salt such as ammonium sulphate, and performing chromatographic procedures such as ion exchange chromatography, affinity chromatography, or the like.

The above description discloses several methods and materials of the present invention. This invention is susceptible to modifications which will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention. All references cited herein are incorporated by reference in their entirety and are hereby made a part of this specification.

EXAMPLES

Having generally described embodiments of the present invention, a further understanding can be obtained by reference to certain specific examples which are provided herein for purposes of illustration only, and are not intended to be limiting.

Example 1

*Cerrena unicolor* IBB 303 was used as enzyme producer. 50 ml of pre-culture mycelium homogenate were added per liter of medium in the shaking flasks, i.e. 2.5 ml were added to a 250-ml Erlenmeyer flasks filled with 50 ml of growth medium containing various lignocellulosic materials (particles size <1 mm). The cultivation temperature was 27° C. and the orbital shaking rate was 150 rpm. The cultivation period was 5-14 days. At the indicated times, 1 ml aliquots were removed from the culture and assayed for enzyme activity in the supernatant. The laccase and MnP yields were 2-123 IU/ml and 0.4-2.1 IU/ml, respectively (Table 1). Mandarin peels and EPR appeared to be the best growth substrates for the production of laccase while walnut pericarp provided the highest MnP activity of the fungus. Moreover, the fungus accumulated high levels of endoglucanase and xylanase activities, 0.8-4.6 IU/ml and 1.4-9.1 IU/ml, respectively.

The media were composed as follows:
a) Pre-culture medium (g/l):
  Glucose—10.0
  $NH_4NO_3$—2.0
  Yeast extract—3.0
  $KH_2PO_4$—0.8
  $K_2HPO_4$—0.2
  $MgSO_4 \times 7H_2O$—0.5
b) The fermentation medium (g/l):
  Lignocellulosic material—40.0
  $NH_4NO_3$—2.0
  Yeast extract—3.0
  $KH_2PO_4$—0.8
  $K_2HPO_4$—0.2
  $MgSO_4 \times 7H_2O$—0.5
  pH—5.5

Endoglucanase (CMCase) activity was assayed according to IUPAC recommendations by mixing 70 µl appropriately diluted samples with 630 µl of low-viscosity carboxymethyl cellulose (1% w/v) in 50 mM citrate buffer (pH 5.0) at 50° C. for 10 min (Ghose, 1987). Xylanase activity was determined by mixing 70 µl appropriately diluted samples with 630 µl of birch wood xylan (Roth 7500) (1% w/v) in 50 mM citrate buffer (pH 5.0) at 50° C. for 10 min (Bailey et al., 1992). Glucose and xylose standard curves were used to calculate the cellulase and xylanase activities. In all assays the release of reducing sugars was measured using the dinitrosalicylic acid reagent method (Miller, 1959). One unit of enzyme activity was defined as the amount of enzyme, releasing 1 µmol of reducing sugars per minute.

Laccase activity was determined by monitoring spectrophotometrically the change in absorbance at 420 nm ($A_{420}$) related to the rate of oxidation of 1 mM 2,2'-azino-bis-[3-ethylbenzthiazoline-6-sulfonate] (ABTS) in 50 mM Na-acetate buffer (pH 4.0). Assays were performed in 1-ml cuvettes at 20±1° C. with 50 µl of adequately diluted spent medium. One unit of activity was defined as the amount of enzyme which leads to the oxidation of 1 µmol of ABTS per minute.

MnP activity was measured at 270 nm by following the formation of $Mn^{3+}$-malonate-complexes (Wariishi et al., 1992). One unit of laccase or MnP activity was defined as the amount of enzyme that leads to the oxidation of 1 µmol of substrate per minute.

TABLE 1

Cerrena unicolor laccase and MnP activities in submerged fermentation of lignocellulosic materials

| Substrate | Laccase (IU/ml) | MnP (IU/ml) | CMCase (IU/ml) | Xylanase (IU/ml) |
|---|---|---|---|---|
| Banana peels | 16 | 0.7 | 4.2 | 4.8 |
| EPR | 116 | 0.4 | 4.6 | 9.1 |
| Mandarin peels | 123 | 1.0 | 2.7 | 5.1 |
| Walnut pericarp | 37 | 2.1 | 2.7 | 3.0 |
| Wheat bran | 78 | 1.2 | 1.8 | 4.5 |
| Wheat straw | 2 | 0.9 | 0.8 | 1.4 |

Example 2

*Cerrena unicolor* IBB 303 was used as enzyme producer. 50 ml of pre-culture mycelium homogenate were added per liter of medium in the shaking flasks, i.e. 2.5 ml were added to a 250-ml Erlenmeyer flasks filled with 50 ml of growth medium. To demonstrate the capability of the selected fungus to produce laccase in absence of cellulase and xylanase secretion due to catabolite repression the following chemically pure sources of carbon were used: glucose, cellobiose, or glycerol. The cultivation temperature was 27° C., the orbital shaking rate 150 rpm. The cultivation period was 5-13 days. At the indicated times, 1 ml aliquots were removed from the culture and assayed for enzyme activity in the supernatant. The laccase yields were 35-78 IU/ml (FIG. 1). Only traces of hydrolytic enzymes activity could be detected in this case.

The media were composed as follows:
a) Pre-culture medium (g/l):
  Glucose—10.0
  $NH_4NO_3$—2
  Yeast extract—3.0
  $KH_2PO_4$—0.8
  $K_2HPO_4$—0.2
  $MgSO_4 \times 7H_2O$—0.5
b) The cultivation medium (g/l):
  Cellobiose/glucose/glycerol/Na-gluconate—15.0
  $(NH_4)_2SO_4$—2.0
  Yeast extract—3.0
  $KH_2PO_4$—0.8
  $K_2HPO_4$—0.2
  $MgSO_4 \times 7H_2O$—0.5
  $CuSO_4 \cdot 5H_2O$—0.13
  pH—5.5

Enzyme activities were measured as described above in Example 1.

Example 3

Figure 2:
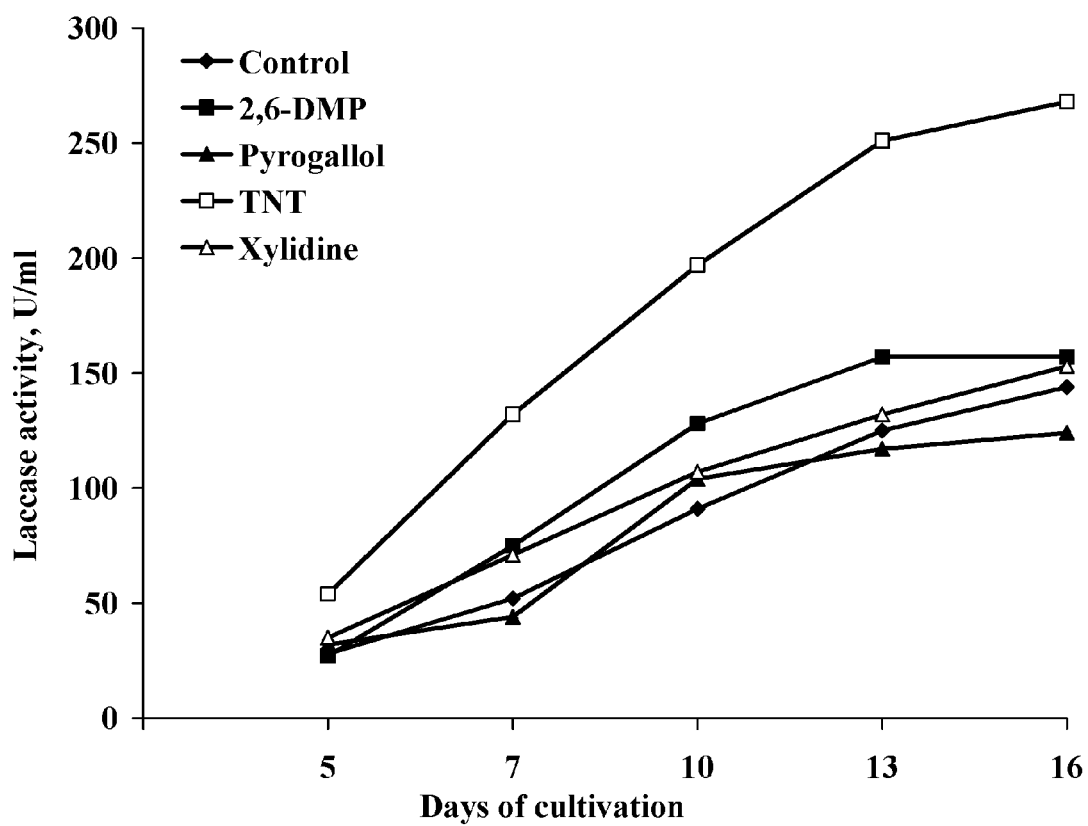
FIG. 2 is a graph showing *Cerrena unicolor* laccase activity in submerged fermentation of mandarin peels in the presence of aromatic compounds.

*Cerrena unicolor* IBB 303 was used as enzyme producer. 50 ml of pre-culture mycelium homogenate were added per liter of medium in the shaking flasks, i.e. 2.5 ml were added to a 250-ml Erlenmeyer flasks filled with 50 ml of fermentation medium containing mandarin peels (particles size <1 mm). To further increase the laccase production one of the following aromatic compounds was supplemented in fermentation medium: 2,6-dimethoxyphenol (2,6-DMP), pyrogallol, 2,4,6-trinitrotoluene, xylidine. The cultivation temperature was 27° C., the orbital shaking rate 150 rpm. The cultivation period was 5-10 days. At the indicated times, 1 ml aliquots were removed from the culture and assayed for enzyme activity in the supernatant. The laccase yield was 124-268 IU/ml (FIG. 2).

The media were composed as follows:
a) Pre-culture medium (g/l):
  Glucose—10.0
  $NH_4NO_3$—2.0
  Yeast extract—3.0
  $KH_2PO_4$—0.8
  $K_2HPO_4$—0.2
  $MgSO_4 \times 7H_2O$—0.5
b) The fermentation medium (g/l):
  Milled mandarin peels—40.0
  $(NH_4)_2SO_4$—4.0
  Yeast extract—3.0
  $KH_2PO_4$—0.8
  $K_2HPO_4$—0.2
  $MgSO_4 \times 7H_2O$—0.5
  $CuSO_4 \cdot 5H_2O$—0.3
  2,6-dimethoxiphenol, pyrogallol, 2,4,6-trinitrotoluene, or xylidine supplement in a final concentration of 0.3 mM, respectively.
  pH—5.5

Enzyme activities were measured as described above in Example 1.

Example 4

Figure 3:
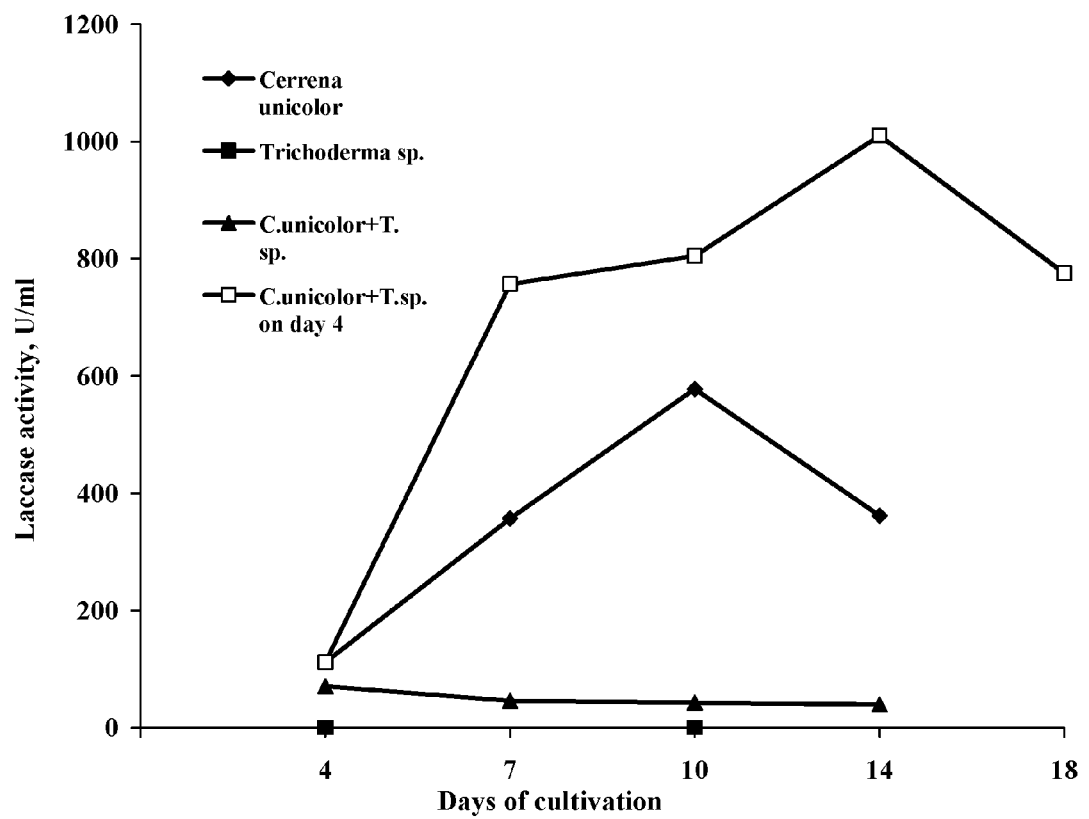
FIG. 3 is a graph showing *Cerrena unicolor* laccase activity in co-cultivation with *Trichoderma* sp on mandarin peels.

*Cerrena unicolor* IBB 303 was used as enzyme producer. 50 ml of pre-culture mycelium homogenate were added per liter of medium in the shaking flasks, i.e. 2.5 ml were added to a 250-ml Erlenmeyer flasks filled with 50 ml of fermentation medium containing mandarin peels (particles size <1 mm). To further increase the laccase yield, *C. unicolor* was co-cultivated with *Trichoderma* sp. from the time of inoculation and after 4 days of submerged fermentation. To promote fungal growth and to direct the target enzyme production, the nutrient medium was supplemented with glycerol to repress cellulase and xylanase synthesis. Moreover, to stimulate laccase production, the nutrient medium was supplemented with 1 mM $CuSO_4.\times5H_2O$ and 0.3 mM 2,4,6-trinitrotoluene. The cultivation temperature was 27° C., the orbital shaking rate 150 rpm. The cultivation period was 5-10 days. At the indicated times, 1 ml aliquots were removed from the culture and assayed for enzyme activity in the supernatant. The laccase yield is 110-219 IU/ml (FIG. 3).

The media were composed as follows:
a) Pre-culture medium (g/l):
  Glucose—10.0
  $NH_4NO_3$—2.0
  Yeast extract—3.0
  $KH_2PO_4$—0.8
  $K_2HPO_4$—0.2
  $MgSO_4\times7H_2O$—0.5
b) The cultivation medium (g/l):
  Milled mandarin peels—40.0
  Glycerol—15.0
  Peptone—3.0
  Yeast extract—3.0
  $KH_2PO_4$—0.8
  $K_2HPO_4$—0.2
  $MgSO_4\times7H_2O$—0.5
  $CuSO_4.\times5H_2O$—0.3
  2,4,6-Trinitrotoluene—0.7
  pH—5.5

Enzyme activities were measured as described above in Example 1.

Example 5

*Cerrena unicolor* IBB 303 was used as enzyme producer. 100 ml of pre-culture mycelium homogenate were added per liter of medium in the shaking flasks, i.e. 5 ml were added to a 250-ml Erlenmeyer flasks filled with 50 ml of fermentation medium containing various concentrations of mandarin peels (particles size <1 mm). To promote fungal growth and to further increase the laccase and MnP yield, the mandarin peels-based nutrient medium was supplemented with additional carbon and nitrogen sources at varying concentrations. Moreover, to stimulate laccase production the nutrient medium was supplemented with $CuSO_4.\times5H_2O$ and 2,4,6-trinitrotoluene. The cultivation temperature was 27° C., the orbital shaking rate 150 rpm. The cultivation period was 5-15 days. At the indicated times, 1 ml aliquots were removed from the culture and assayed for enzyme activity in the supernatant. The laccase and MnP yields are 203-1162 IU/ml and 3.1-9.4 IU/ml, respectively (Table 2).

The media were composed as follows:
a) Pre-culture medium (g/l):
  $NH_4NO_3$—2.0
  Yeast extract—3.0
  $KH_2PO_4$—0.8
  $K_2HPO_4$—0.2
  $MgSO_4\times7H_2O$—0.5
b) The cultivation medium (g/l):
  Milled mandarin peels—40.0 or 60.0
  Glycerol—0 or 15.0
  Peptone—3.0 or 9.0
  Yeast extract—3.0
  $KH_2PO_4$—0.8
  $K_2HPO_4$—0.2
  $MgSO_4\times7H_2O$—0.5
  $CuSO_4.\times5H_2O$—0.3
  2,4,6-Trinitrotoluene—0.7
  pH—5.5

Enzyme activities were measured as described above in Example 1.

TABLE 2

*Cerrena unicolor* laccase and MnP activities in submerged fermentation of mandarin peels in the presence of additional carbon and nitrogen sources

| Media variants | Laccase (IU/ml) | MnP (IU/ml) |
|---|---|---|
| 4% MP + 0.3% peptone | 203 | 3.1 |
| 4% MP + 0.3% peptone + 1.5% glycerol | 268 | 9.1 |
| 4% MP + 0.9% peptone | 341 | 3.3 |
| 4% MP + 0.9% peptone + 1.5% glycerol | 760 | 9.4 |
| 6% MP + 0.3% peptone | 321 | 5.7 |
| 6% MP + 0.3% peptone + 1.5% glycerol | 575 | 8.1 |
| 6% MP + 0.9% peptone | 546 | 4.7 |
| 6% MP + 0.9% peptone + 1.5% glycerol | 1162 | 7.8 |

Comparative Example

Embodiments of the present invention afford a considerable increase in the laccase and manganese peroxidase activity and productivity compared with all the methods known hitherto. Whereas a laccase activity of the order of 500-600 IU/l is obtained after cultivating *C. unicolor* for 14 days in a culture medium supplemented with inducers (veratric acid, ferulic acid or xylidine) in accordance with Rogalski J. et al., "Immobilization of laccase from *Cerrena unicolor* on controlled porosity glass," *J. Mol. Catalysis B: Enzymatic*. 1999, 6, 29-39), and whereas the MnP activity is of the order of 30-300 U/l when the culture medium is supplemented with inductors (Rogalski J., Dawidowicz A., Jozwik E., Leonowicz A. Immobilization of laccase from *Cerrena unicolor* on controlled porosity glass. *J. Mol. Catalysis B: Enzymatic*. 1999, 6, 29-39; Gil P. K., Arora D. S. Effect of culture conditions on manganese peroxidase production and activity by some white rot fungi. *J. Ind. Microbiol. Biotechnol*. 2003, 30, 28-33), the laccase and MnP activities according to the embodiments described herein quite unexpectedly reached 100,000-1,000,000 IU/l and 2,000-9,000 IU/l, respectively, after 7-14 days of *C. unicolor* cultivation in which growth medium was supplemented with selected lignocellulosic material.

What is claimed is:

1. A method of producing ligninolytic enzymes comprising:
  incubating a fungal strain of *Cerrena unicolor* in a fermentation system comprising growth medium which comprises a lignocellulosic material, wherein the fungal strain of *Cerrena unicolor* is IBB 303; and cultivating the fungal strain in the fermentation system under conditions wherein the fungus expresses the ligninolytic enzymes.

2. The method of claim 1, wherein the fermentation system is a submerged fermentation system.

3. The method of claim 1, further comprising inoculating a starter culture with the fungal strain of *Cerrena unicolor* capable of expressing ligninolytic enzymes.

4. The method of claim 1, wherein the lignocellulosic material is mandarin peel, ethanol production residue, walnut pericarp, wheat bran, wheat straw, or banana peel.

5. The method of claim 1, wherein the ligninolytic enzymes comprise cellulase, xylanase, laccase, or manganese-dependent peroxidase.

6. The method of claim 1, further comprising recovering the ligninolytic enzymes from said fermentation system.

7. The method of claim 6, wherein the recovered ligninolytic enzyme is laccase having an activity of 100,000 to 1,000,000 IU/l.

8. The method of claim 6, wherein the recovered ligninolytic enzyme is manganese-dependent peroxidase having an activity of 2,000 to 9,000 IU/l.

9. The method of claim 1, further comprising co-cultivating the fungal strain with *Trichoderma* sp.

10. The method of claim 1, wherein the lignocellulosic material is mandarin peel and expression of laccase is enriched among the expressed ligninolytic enzymes.

11. The method of claim 1, wherein the lignocellulosic material is walnut pericarp and expression of manganese-dependent peroxidase is enriched among the expressed ligninolytic enzymes.

12. The method of claim 1, wherein the fermentation system further comprises glycerol and wherein expression of cellulase and xylanase is repressed compared to enhanced expression of laccase or manganese-dependent peroxidase.

13. The method of claim 1, wherein the fermentation system further comprises 2,4,6-trinitrotoluene and expression of laccase is increased among the expressed ligninolytic enzymes.

14. The method of claim 1, wherein the fermentation system comprises mandarin peel, glycerol, peptone, copper sulphate, and trinitrotoluene.

* * * * *